Figure 1A:
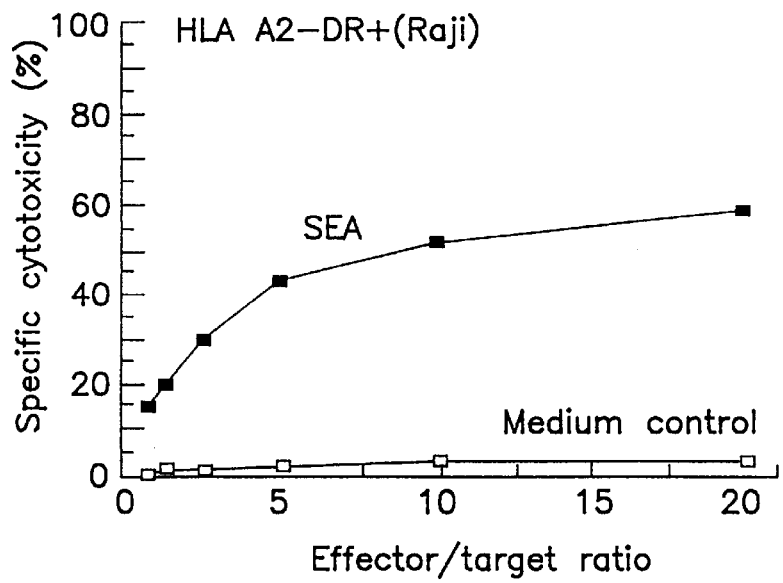

US006042837A

United States Patent [19]
Kalland et al.

[11] Patent Number: 6,042,837
[45] Date of Patent: *Mar. 28, 2000

[54] METHODS OF STAPHYLOCOCCAL ENTEROTOXIN DIRECTED CELL-MEDIATED CYTOTOXICITY (SDCC)

[76] Inventors: Terje Kalland, Odlarevägen 31, S-240 21 Löddeköpinge; Gunnar Hedlund, Mårtenstorget 10 C, S-223 51 Lund; Mikael Dohlsten, Lilla Södergatan 6, S-223 53 Lund; Peter Lando, Sofielunds vägen44, S-214 34 Malmö, all of Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/596,555

[22] Filed: Feb. 5, 1996

Related U.S. Application Data

[62] Division of application No. 08/467,855, Jun. 6, 1995, abandoned, which is a continuation of application No. 08/097, 940, Jul. 26, 1993, abandoned, and a division of application No. 07/689,799, filed as application No. PCT/SE90/00592, Sep. 14, 1990, abandoned.

[30] Foreign Application Priority Data

Sep. 20, 1989 [SE] Sweden .................................. 8903100

[51] Int. Cl.$^7$ .................................................. A61K 39/085
[52] U.S. Cl. ................................. 424/237.1; 424/234.1; 424/243.1; 530/350
[58] Field of Search ............................. 424/185.1, 243.1, 424/244.1, 237.1, 234.1; 530/350, 300

[56] References Cited

U.S. PATENT DOCUMENTS

| | | |
|---|---|---|
| 3,627,644 | 12/1971 | Okamoto et al. . |
| 4,237,224 | 12/1980 | Cohen et al. . |
| 4,268,434 | 5/1981 | Higerd et al. . |
| 4,677,064 | 6/1987 | Mark et al. ................................. 435/68 |
| 4,681,870 | 7/1987 | Balint, Jr. et al. . |
| 4,689,222 | 8/1987 | McMichael . |
| 4,699,783 | 10/1987 | Terman et al. . |
| 4,791,101 | 12/1988 | Adolf .......................................... 514/2 |
| 4,816,441 | 3/1989 | Zeuthen et al. ............................. 514/12 |
| 4,980,160 | 12/1990 | Goldberg et al. . |
| 5,091,091 | 2/1992 | Terman . |
| 5,362,490 | 11/1994 | Kurimoto et al. ...................... 424/85.5 |

FOREIGN PATENT DOCUMENTS

| | | |
|---|---|---|
| 355047 | of 0000 | European Pat. Off. . |
| 2828947 | of 0000 | Germany . |
| 8702602 | of 0000 | WIPO . |
| 9000592 | of 0000 | WIPO . |
| 9100342 | of 0000 | WIPO . |
| 9201470 | of 0000 | WIPO . |
| WO 8404887 | 12/1984 | WIPO . |
| WO 8802632 | 4/1988 | WIPO . |
| WO 890619 | 10/1989 | WIPO . |
| WO89/09619 | 10/1989 | WIPO . |
| WO91/10680 | 7/1991 | WIPO . |

OTHER PUBLICATIONS

Murphy et al., Staphylococcal Protein A Adsorption in neoplastic disease: Analysis of physicochemical aspects. *Mol. Biother.*, 1 (1989) 186–207.

Solal–Celigny et al., Effects of ex–vivo plasma absorption over protein A sepharose in acute leukemia. *Leukemia Research* 10(6) (1986) 643–49.

Platsoucas et al., Immunomodulation of human leucocytes by staphylococcal enterotoxin A; augmentation of natural killer cells and induction of suppressor cells. *Cell. Immunol.* 97 (1986) 371–385.

Smith et al., Staphylococcal aureus protein A induces the production of interferon–alpha in human lymphocytes and interferon–alpha/beta in mouse spleen cells. *J. Immunol.* 13–0 (1983) 773–776.

Carlsson et al., Staphylococcal protein A (SpA) does not induce production of interferon–gamma in human mononuclear blood cells. *Cell. Immunol.* 86 (1984) 136–144.

Branda et al., Further characterization of the in vitro tumoricidal activity of staphylococcal protein A. *Cancer Research* 46 (1986) 2610–2613.

Weiss R., Immunotherapy for feline leukemia, using staphylococcal protein A or heterologous interferons: immunopharmacologic actions and potential use. *J. Am. Vet. Med. Assoc.*, 192 (Mar. 1988), 681–684.

Garcia–Penarrubia et al. Selective proliferation of natural killer cells among monocyte–depleted peripheral blood mononuclear cells as a result of stimulation with staphylococcal enterotoxin B. *Infection and Immunity*, 57 (Jul. 1989) 2057–2065.

Fischer et at. Binding of staphylococcal enterotoxin A to HLA–DR on B cell lines. *J. Immunol.* 142 (1989) 3151–3157.

Carswell et al. An endotoxin–induced serum factor that causes necrosis of tumors. *Proc. Natl. Acad. Sci.*, 92 (9) (1975) 3666–3670.

Fast et al. Toxic shock syndrome–associated staphylococcal and streptococcal pyrogenic toxins are potent inducers of tumor necrosis factor production. *Infection and Immunity*, 57 (Jan. 1989) 291–294.

Schrezenmeir and Fleischer. Mitogenic activity of staphylococcal protein A is due to contaminating staphylococcal enterotoxins. *J. Immunol. Meth.* 105 (1987) 133–137.

Carlsson et al. Binding of staphylococcal enterotoxin A to accessory cells is a requirement for its ability to activate human T cells. *J. Immunol.* 140 (1988) 2484–2488.

Scheglovitova et al. Inteferon production and natural killer activity induced by staphylococcal enterotoxins in mouse spleen cells. *Vopr. Virusol.* 33 (3) (May–Jun. 1988) 305–309.

(List continued on next page.)

Primary Examiner—Thomas M. Cunningham
Attorney, Agent, or Firm—Fulbright & Jaworski, L.L.P.

[57] ABSTRACT

Methods of staphylococcal enterotoxin directed cell-mediated cytotoxicity (SDCC), including methods of lysing malignant cells expressing MHC Class II antigens using SDCC, by the administration of staphylococcal enterotoxin to a living body.

2 Claims, 3 Drawing Sheets

OTHER PUBLICATIONS

Terman and Bertram. Antitumor effects of immobilized protein A and staphylococcal products: Linkage between toxicity and efficacy, and identification of potential tumoricidal reagents. *Eur. J. Clin. Oncol.* 21 (1985) 1115–1122.

Abstract No. 84048345, Biological Abstracts, Journal Article.

Abstract No. 88075810, Biological Abstracts, Journal Article.

Abstract No. 88087362, Biological Abstracts, Journal Article.

Hamaoka, T., *Immunology Today*, vol. 8, No. 9, 1987, "Phenotypically and Functionally Distinct T–Cell Subsets in Anti–Tumor Responses".

Fleischer, B., In: *Cellular Immunology*, 120: 92–101, 1989.

Roitt, et al., *Immunology*, pp. 18.7, 13.3, 23.8, 23.9.

Fraser, J.D., In: *Nature*, 339: 221–223, May, 1989.

Matthes, M., et al., In: *European Journal of Immunology*, 18: 1733–1737, 1988.

Stuart, P.M. et al., *Journal of Immunology*, 142: 3392–3399, 1989.

Nauts, "Beneficial Effects of Immunotherapy (Bacterial Toxins) on Sarcoma of the Soft Tissues, Other than Lymphosarcoma", Cancer Research, Inc., New York, NY, pp. 1–25 & 205–219, 1975.

Coley, *Treatment of inoperable Sarcoma*, "Surgical Section", Pro Royal Soc. Med, 1910/1911; 3:1–48.

Hedlund, *Cellular Immunology*, 129:426–434, 1990.

Paul, W.F. (ed), *Fundamental Immunology*, 3rd Edition, pp. 80–81, 403–405, 1038–1040 & 1296, 1993.

Held, et al., *Immunology Today*, 15(4): 184–193, Apr., 1994, "Superantigens and retroviral infection; insights from mouse mammary tumor virus".

Wallgren et al., *Blood*, 82:1230–1238, 1993.

Dohlsten, M., *Immunology*, 79:520–527, 1993.

Belfrage, et al. *Cancer Immunology*, 38:265–271, 1994.

White, J. et al., *Cell*, 56:27–35, Jan., 1989.

Hedlund, et al., *Cancer Immunol. Immunother*, 36: 89–93, 1993.

Kappler, et al., *Science*, 244: 811–813, 1989.

Shcheglovitova, et al., "Non–Specific Anti–tumour Activity of Staphylococcal Exterotoxins"—Paper.

Shcheglovitova, et al., "The Effect of Staphylococcal Exterotoxins A–Sensitized Spleen Cells on the Metastatic Spreading of Lewis Lung Carcinoma in Mice" Eksp. Onkol. 11:54–56 (1989).

Shcheglovitova, et al., "The Effect of Staphylococcal Exterotoxins A on the Development of Lewis Lung Carcinoma in Mice"—Eksp. Onko 11:73–79 (1989.

Bergdoll, M., In: *Staphylococci and Staphyloccocal Infections*, C.S.F. Easman and C. Adam (eds) Acad. Press, New York, pp. 559–598, 1983.

Carlsson, R., et al., *Cell. Immunology*, 96:175–181, 1985.

Fischer, H., et al., *The J. of Immunol.*, 142: 3151–3157, May, 1989.

Fischer, J., et al., *The J. of Immunol.*, 144: 4663–4669, Jun., 1990.

Guillemot, F. et al, In: *Molecular Immunology*, B.J. Hames and D.M. Glover (eds), IRL Press, Oxford, pp. 81–143.

Lando, P., et al., *Scand. J. Immunol.*, 31: 133–138, 1990.

Langford, M., et al., *Infection and Immunol.*, 22, No.1: 62–68, Oct., 1978.

Mollick, J., et al. *Science*, 244: 817–820, 1989.

*J. Immunology*, 122:549–554, 1979.

*J. Exp. Med.*, 155:445, 1982.

*Cancer Chemother Res.*, 3:325, 1972.

*Cancer Res*, 15:38, 1985.

Lando, P. et al., *Scand. J. Immunol.*, "The TCR–CD3 Complex is required for activation of human lymphocytes with Staphlococcal Exterotoxins A", 1989.

Dellabona et al., *Cold Springs Haub. Symp. Quant. Biol.*, 54:t (1989) 1:373.

Blackman et al., *Immunol. Rev.*, 101:5–19, (1988).

Beardsley, *Sci. Am.*, 261:1, 1989.

Kappler, et al, *Cold Springs Haub. Symp. Quant. Biol.*, 54:t (1989) 1:401.

Rich et al., *Trans. Am. Clin. Climatol. Assoc.*, 101:15, 1989.

Nauts, *Beneficial Effects of Immunotherapy (Bacterial Toxins) on Sarcoma of the Soft Tissues*, Other than Lymphosarcoma, Cancer Research Institute Inc., New York, NY, 1975, pp. 1–25 and 205–219.

Fraser, J.D. , In: *Nature*, 339: 221–223, May 1989.

Stuart, M. P., et al., In: *The Journal of Immunology*, 142: 3392–3393, May, 1989.

Carlsson, R., et al., *Cell. Immunol.*, 96: 175–181, 1985.

Fischer, W., et al., *The J. of Immunol.*, 142: 3151–3157, May, 1989.

Fischer, W., et al., *The J. of Immunol.*, 144: 4663–4669, Jun., 1990.

Guilemot, F. et al., In: *Molecular Immunology*, B.J. Hames and D.M. Glover (Eds), IRL Press, Oxford, 1988, pp. 81–143.

Langford, M., et al., *Infection and Immunol.*, 22,No.1: 62–68, Oct. 1978.

Mollick, J., et al., *Science*, 244: 817–820, 1989.

White, J. et al., *Cell*, 56: 27–35, Jan., 1989.

Scheglovitova et al, Vopr. Virusol. 32(3):327–329, "Use of enterotoxins adsorbed on filters for induction of human immune interferon", 1987.

Alakhov et al., Biotechnol. Appl. Biochem. 10:563–7, "The effect os Staphylococcus aureus enterotoxin A on proliferation of lymphoid and nerve cells", 1988.

Andersson et al., J. Immunol. Methods 123:233–240, "Characterization of individual tumor necrosis factor alpha and beta–producing cells after polyclonal T cell activation", 1989.

Johnson et al., Int. Arch. Aleergy Appl.Immunol. 87:87–90, "Potent mitogenic activity of staphylococcal enterotoxin A requires induction of interleukin 2", 1988.

Office Action in 08/596,555 with attachments.

Communication regarding EPO Application No. 91 903 963.6–2110 (David S. Terman et al.).

Opposition to EP–B–444186 (90914564.1) by David A. Terman.

Reply to EP–B–444186 (90914564.1) (with attachments).

Correspondence to European Patent Office from David S. Terman.

D. Terman et al., "Preliminary Observations of the Effects of Breast Adenocarcinoma of Plasma Perfused Over Immobilized Protein A," New Eng. J. Med., 305:1195–1200 (1981).

F. Chu et al., "Purification and Characterization of Staphylococcal Enterotoxin A," Biochem., 5:3281 (1966).

M. Bergdoll et al., "Identification of a New Enterotoxin as Enterotoxin C,"J. Bacteriol., 90:1481 (1965).

C. Borja and M. Bergdoll, "Purification and Partial Characterization of Enterotoxin C Produced by *Staphylococcus aureus* Strain 137," Biochem., 6:1467 (1967).

R. Avena and M. Bergdoll, "Purification and Some Physiochemical Properties of Enterotoxin C, *Staphylococcus aureus* Strain 361," Biochem., 6:1474 (1967).

E. Schantz et al., "Purification and Some Chemical and Physical Properties of Staphylococcal Enterotoxin A." Biochem., 11:360 (1972).

E. Schantz et al., "Purification of Staphylococcal Enterotoxin B," Biochem., 4:1011 (1965).

H–C. Chang and M. Bergdoll, "Purification and Some Physiochemical Properties of Staphylococcal Enterotoxin D," Biochem., 18:1937 (1979).

C. Borja et al., "Purification and Some Physicochemical Properties of Staphylococcal Enterotoxin E," J. Biol. Chem., 247:2456 (1972).

M. Dayhoff (ed.), Data Section, in *Atlas of Protein Sequence Structure* 5:D227, National Biomedical Research Foundation, Washington, D.C. (1972).

M. Bergdoll et al., "Enterotoxin Synthesis by the Staphylococci," In *Recent Advances in Staphylococcal Research* (W.W. Yotis, ed.), Ann. N.Y. Acad. Sci., 236:307.

J. Iandolo, "Genetic Analysis of Extracellular Toxins of *Staphylococcus aureus*," Ann. Rev. Microbiol., 43:375 (1989).

M. Bergdoll et al., "Staphylococcal Enterotoxin B, III. The Physiocochemical Properties and the N– and C–Terminal Amino Acid Sequences," Arch. Biochem. Biophys., 112:104 (1965).

I. Huang et al., "Amino Acid Composition and Terminal Amino Acids of Staphylococcal Enterotoxin C," Biochem., 6:1480 (1967).

M. Bergdoll et al., "Chemistry of the Staphylococcal Enterotoxins," J. Agric. Food Chem., 22:9 (1974).

D. Blomster–Hautamaa et al., "Preparation of Toxic Shock Syndrome Toxin–1," Methods in Enzymology 165:37 (1988).

M. Bergdoll et al., "Identification of Enterotoxin E," Infect. Immun., 4:593 (1971).

M. Bergdoll, "Enterotoxins," in *Staphylococci and Staphylococci Infections* (C.S.F. Easmon and C. Adlam, eds.), pp. 559–598 (1983).

J. Freer and J. Arbuthnott, "Toxins of *Staphylococcus aureus*," Pharmac. Ther., 19:55 (1983).

L. Johnson et al., "Streptococcal Pyrogenic Exotoxin Type A (scarlet fever toxin) is related to *Staphylococcus aureus* Enterotoxin B," Mol. Gen. Genet., 203:354 (1986).

W. Pearson and D. Lipman, "Improved Tools for Biological Sequence Comparison," Proc. Nat'l. Acad. Sci. USA, 85:2444 (1988).

J. Lipman and W. Pearson, "Rapid and Sensitive Protein Similarity Searches," Sci., 227:1435 (1985).

C. Janeway, Jr. et al., "T–Cell Responses to Mls and to Bacterial Proteins that Mimic its Behavior," Immunol. Rev., 107:61–88.

J. Yagi et al., "Bacterial Proteins That Mediate the Association of a Defined Subset of T Cell Receptor:CD4 Complexes With Class II MHC," J. Immunol., 144:892–901.

H. Stewart et al., in *Atlas of Tumor Pathology*, Armed Forces Institute of Pathology, Washington, D.C., pp. 38, 355 (1959).

J. Kidd et al., "A Transplantable Rabbit Carcinoma Originating in a Virus–Induced Papilloma and Containing the Virus in Masked or Altered Form," J. Exp. Med., 71:813–838 (1940).

T. Maniatis et al., *Molecular Cloning: A Laboratory Manual*, Cold Spring Harbor Laboratory, New York (1982).

J. Betley and J. Mekalanos, "Nucleotide Sequence of the Type A Staphylococcal Enterotoxin Gene," J. Bacteriol., 170:34 (1987).

I. Huang et al., "Complete Amino Acid Sequence of Staphylococcal Enterotoxin A," J. Biol. Chem., 262:7006 (1987).

M. Betley et al., "Staphylococcal Enterotoxin A Gene is Associated With a Variable Genetic Element," Proc. Natl. Acad. Sci. USA 81:5179 (1984).

M. Gaskill and S. Khan, "Regulation of the Enterotoxin B Gene in *Staphylococcus aureus*," J. Biol. Chem., 263:6276 (1988).

C. Jones and S. Khan, "Nucleotide Sequence of the Enterotoxin B Gene from *Staphylococcus aureus*," J. Bacteriol., 166:29 (1986).

I. Huang and M. Bergdoll, "The Primary Structure of Staphylococcal Enterotoxin B," J. Biol. Chem., 245:3518 (1970).

G. Bohach and P. Schlievert, "Expression of Staphylococcal Enterotoxin $C_1$ in *Escherichia coli*," Infect. Immun., 55:428 (1987).

G. Bohach and P. Schlievert, "Nucleotide Sequence of the Staphylococcal Enterotoxin $C_1$ Gene and Relatedness to Other Pyrogenic Toxins," Mol. Gen. Genet., 209:15 (1987).

J. Couch et al., "Cloning and Nucleotide Sequence of the Type E Staphylococcal Enterotoxin Gene," J. Bacteriol., 170:2954 (1988).

B. Krieswirth et al., "The Toxic Shock Syndrome Exotoxin Structural Gene is Not Detectably Transmitted by a Prophage," Nature 305:709 (1983).

J. Cooney et al., "Molecular Cloning and Genetic Analysis of the Determinant for Gamma–Lysin, a Two–component Toxin of *Staphylococcus aureus*," J. Gen. Microbiol., 134:2179 (1988).

M. Friedman et al., "Induction of Mutants of *Staphylococcus aureus* 100 With Increased Ability to Product Enterotoxin A," J. Bacteriol., 106:289 (1971).

D. Terman, "Staphylococcal Protein A Neoplastic Disease," J. Biol. Response Modifiers 3:316 (1984).

D. Terman and J. Bertram., "Antitumor Effects of Immobilized Protein A and Staphylococcal Products: Linkage Between Toxicity and Efficacy, and Identification of Potential Tumoricidal Reagent," Eur. J. Cancer Clin. Oncol., 21:1115 (1985).

D. Terman, "Immunoadsorbents in Automimmune and Neoplastic Diseases," Plasma Ther. Transfus. Technol., 4:415 (1983).

D. Terman, "Protein A and Staphylococcal Products in Neoplastic Disease," CRC Crit. Rev. Oncol./Hematol., 4:103 (1985).

D. Terman, "Immobilized Enzymes and Cells," in *Methods in Enzymology*, vol. 137 (K. Mosbach, ed.), Acadmic Press, San Diego, pp. 496–515 (1988).

J. Mikolàšek, "Direct Evidence for Rejection of Tumour Allografts in *S. pyogenes* Toxins–Treated Mice Correlated with Antistreptolysin O Level in Serum," Neoplasma 19:507 (1972).

O. Shcheglovitova et al., Eskp Onkol., 9(1):28–30 (1987), cited in: Biol. Abstr., 84(5):AB–685, Ref. 48345 (1987); O.N.

Shcheglovitova et al., Eksp Onkol., 11(2):54–57 (1989), cited in: Biol. Abstr., 88(8):AB–700, Ref. 87362 (1989); and O.N.

Shcheglovitova et al., Eksp Onkol., 11(1):73–74 (1989), cited in: Biol. Abstr., 88(7):AB–639, Ref. 75810 (1989).

P. Garcia–Peñarrubia et al., "Selective Proliferation of Natural Killer Cells Among Monocyte–Depleted Peripheral Blood Mononuclear Cells as a Result of Stimulation with Staphyococcal Enterotoxin B," Infect. and Immun., 57:2057 (1989).

E. Carswell et al., "An Endotoxin–induced Serum Factor That Causes Necrosis of Tumors," Proc. Nat. Acad. Sci. USA 72:3666 (1975).

D. Fast et al., "Toxin Shock Syndrome–Associated Staphylococcal and Pyrogenic Toxins Are Potent Inducers of Tumor Necrosis Factor Production," Infect. Immun., 57:291 (1989).

C. Platsoucas et al., "Immunomodulation of Human Leukocytes by Staphylococcal Enterotoxin A: Augmentation of Natural Killer Cells and Induction of Suppressor Cells," Cellular Immunol., 97:371 (1986).

K. Newell et al., "In vivo T–cell Activation by Staphylococcal Enterotoxin B Prevents Outgrowth of a Malignant Tumor," Proc. Natl. Acad. Sci. USA 88:1074 (1991).

J. Kappler et al., "Vβ–Specific Stimulation of Human T Cells by Staphylococcal Toxins," Science 244:811–813 (1989).

H. Schrezenmeier and B. Fleischer, "Mitogenic Activity of Staphylococcal Protein A is Due to Contaminating Staphylococcal Enterotoxins," J. Immun. Meth., 105:133 (1987).

J. Sjöquist et al., "Protein A Isolated From *Staphylococcus aureus* After Digestion With Lysotaphin," Eur. J. Biochem., 29:572 (1972).

J. Balint, Jr. et al., "Detection, Isolation and Characterization of Staphylococcal Enterotoxin B in Protein A Preparations Purified by Immunoglobulin G Affinity Chromatography," J. Immun. Meth., 116:37 (1989).

Letter of Aug. 27, 1998 to European Patent Office by Opponent David Terman vs. Propietor Pharmacia & Upjohn AB re Opponent's Comments in Response to Invitation to File Observations on the Patentee's Submissions, re. Opposition to European Patent No. EP–B–444186 (909124564.1).

List of references accompanying Dr. Terman's Aug. 27, 1998 letter to the European Patent Office re Opponent's Comments in Response to Invitation to File Observations on the Patentee's Submissions, re Opposition to European Patent No. EP–B–444186 (90914564.1).

Todd et al., Toxic Shock Syndrome Associated with Phage––Group I Staphylococci Lancet 2: 116–120 (1978).

Shands et al., Toxic Shock Syndrome in Menstruating Woman: Association with Tampon Use and Staphylococcus Aureus and Clinical Features in 52 Cases New Engl, J. Med. 303 1436–1441 (1980).

Fisher et al., Cardio–respiratory Failure in Toxic Shock Syndrome: Effect of Dobutamine Critical Care Medicine 13: 160–165 (1985).

Bergdoll et al., A New Staphylococcus Enterotoxin, Enterotoxin F, Associated with the Toxic Shock Syndrome Staphylococcus aureus Isolates Lancet 2 1017–1021 (1981).

Willoughby et al., The Toxic Shock Syndrome and Streptococcal Pyrogenic Exotoxins Ann. Int. Med. 98: 559 (1983).

Cone et al., Clinical and Bacteriological Observations of a Toxic Shock–Like Syndrome due to Streptococcus Pyrogenes New Engl. J. Med. 317: 146–148 (1987).

Stevens et al., Severe Group A Streptococcal Infections Associated with a Toxic Shock–like Syndrome and Scarlet Fever Toxin A New Engl J. Med 32: 321: 1–7 (1989).

Schilievert, PM Staphylococcal Enterotoxin B and Toxic Shock Syndrome Toxin–1 are Significantly Associated with Non–Menstrual TSS Lancet 1: 1149–1150 (1986).

Johnson et al., Mol. Gen. Genet. 203, 354 to 356 (1986).

Borja et al., Biochemistry vol. 6, No. 5, pp. 1467 to 1473, 1967.

Elsberry et al., Hemodynamics of Staphylococcal B Enterotoxaemia and Other Types of Shock in Monkeys J. Applied Physiology 27 164–169.

Liu et al., Cardiovascular and Vomiting Responses to a Lethal Intravenous Dose of Staphyloenterotoxin A in Rhesus Monkeys J Med Primatol. 5: 353–359 (1976).

Eur. J. Immunogenetics 19: 181–285 (1992).

Acolla RJ et al., J. Exp. Med. 157: 1053–1058 (1983).

Kravath et al., Gamma Ray–induced Loss of Expression of HLA and Glyoxalase I Alleles in Lymphoblastoid Cells Proc. Natl. Acad. Sci. USA 77: 4251–4255 (1980).

Acolla et al., J. Exp. Med. 162: 1117–1113 (1985).

Acolla et al., J. Exp. Med. 164: 369–374 (1986).

Shoemaker et al., Development of Human Tumour Cell Line Panels for use in Disease–Oriented Drug Screening in T. Hall editor Prediction of Response to Cancer Therapy Alan Liss N.Y. pp. 265–286 (1988).

Paull K.D. et al., J. Natl. Cancer Inst. 81: 1088–1092 (1989).

Alley M.C. et al., Cancer Res. 48:589–601 (1988).

Scudiero D.A. et al., Cancer Res. 48: 4827–4833 (1988).

Developmental Therapeutics Program Division of Cancer Treatment, National Cancer Institute Proceedings of Workshop on "Selection, Characterisation and Quality Control of Human Tumour Cell Lines from the NCI's New Drug Screening Program" Bethesda, MD May 27–28, 1–73 (1987).

Boyd M.R. Status of NCI preclinical antitumour drug discovery screen in De Vita V.T., Hellman S., Rosenberg S.A., eds Cancer: Principles and Practice of Oncology Updates, vol. 3, No. 10, Lippincott, Phila. 1–12 (1989).

Rooney C., et al., J. Natl. Cancer Inst. (1986).

Sausville E.A. in Anticancer Drug Development Guide: Preclinical Screening, Clinical Trials and Approval B. Teicher editor, Human Press, Totowa, N.J.

METHODS OF STAPHYLOCOCCAL ENTEROTOXIN DIRECTED CELL-MEDIATED CYTOTOXICITY (SDCC)

This application is a division of U.S. patent application Ser. No. 08/467,855, filed Jun. 6, 1995 (now abandoned), which is a continuation of Ser. No. 08/097,940, filed Jul. 26, 1993 (now abandoned), and a division of Ser. No. 07/689, 799, filed Jul. 18, 1991 (now abandoned) which is a 35U.S.C. 371 national application of PCT/SE90/00592 filed Sep. 14, 1990.

The present invention concerns a new agent and a new method for the activation of T cells. Specifically the invention concerns a new agent and method for treating certain cancer forms and autoimmune processes.

BACKGROUND OF THE INVENTION

MHC antigens or transplantation antigens, which in man are also called HLA antigens, play an essential part in T cell activation and the concomitant immune response. Thus e.g. protein antigens are dependent on interactions with MHC antigens for presentation to and activation of T cells during a normal immune response. Likewise, MHC dependent presentation of autoantigens are of key importance in T cell dependent autoimmune processes.

A certain type of MHC antigens, i.e. the so called MHC class II antigens are expressed by a variety of normal cells either constitutionally or after activation (1). Among tumor cells, malignancies of the haematopoietic system commonly express MHC class II molecules. Although MHC class II antigens are not restricted to tumor cells, they may constitute an attractive target for therapy since most normal cells would be spared.

A potent agent capable of eliminating MHC class II antigen expressing cells may therefore be useful both for interruption of autoimmune processes and for the destruction of certain malignant cells.

SUMMARY OF THE INVENTION

Accordingly, the present invention concerns a method of treating malignancies involving cells expressing MHC class If antigens, said method comprising administering to a living body a composition including a substance making said cells targets for cytotoxic T cells.

The invention also comprises a pharmaceutical composition for treating these malignancies. The composition includes a substance making said cells targets for cytotoxic T cells.

The substance should have the ability of activating the cytotoxic T cells, redirect them to MHC class II antigens irrespective of nominal specificity and thereby inactivate or lyse the MHC class II expressing cells.

According to the invention it has been found that a preferred substance is of bacterial origin and has the ability to direct T cells to lyse the target MHC class II antigen expressing cell. It is believed that the substance should interact with parts of the T cell receptor complex (TCR) and, more specifically, particular sequences in the T cell receptor V beta chains. Preferably the substance or bacterial structure is selected from the group comprising of staphylococcal enterotoxins, SE's, such as SEA, SEB, SEC, SEC1, SEC2, SEC3, SED or SEE, toxoids active fragments or peptides of these enterotoxins and substances having essentially the same mod: of action, such as other bacterial products from staphylococcal strains e.g. Toxic shock syndrome toxins (TSST-1) and bacterial exoproteins produced from various other strains, e.g. streptococcal exoproteins and proteins produced by mycoplasma arthritidis, which have similar capacity to interact with certain TCR V-beta sequences. Genetically or chemically modified substances based on the above mentioned structures could also be used.

An example of a substance which does not fall within the scope of the invention is protein A. This protein emanates from Staphylococcus but it is both structurally and functionally different from the staphylococcal entertoxins.

Staphylococcus entertoxins (SE), which are produced by Gram positive bacteria are a family of molecules of protein structure, that are commonly known for causing food poisoning (2). They are also potent T cell mitogens causing T cell activation and concomitant production of lymphokines (3–5). However, SE unlike most mitogens are strictly dependent on the presence of accessory cells expressing MHC class II molecules (6,7).

Moreover, strong circumstantial evidence has been presented that SEA directly interacts with certain T cell receptor families during their activation of lymphocytes (9,9).

It has been previously suggested (WO-Al-89/09619) to sue SEA for the treatment of cancer. According to this publication, however, SEA is used for the treatment of blood in vitro (=outside the patients body), and the SEA is removed before the activated cells are reinfused to the patient, whereas the discovery on which the present invention is based discloses that SEA and functionally similar agents can act as bifunctional crosslinkers in vitro. Activating and bringing T cells to tumor cells in the body can be of potential use for the in vivo treatment of certain types of cancer and autoimmune diseases.

The agent according to the present invention is preferably in the form of a pharmaceutical composition comprising the substance, together with a pharmaceutically acceptable vehicle or carrier.

The composition is furthermore preferably administered parenterally, and should thus include those adjuvants which are commonly used within this field Thus the enterotoxin or fragment thereof could be administered in the form of lipid emulsions, or combined with human serum albumin or mixtures of amino acids. The amount of the active component of the composition can vary within broad ranges e.g. 1 ng–100 mg.

In addition to systemic administration it is also possible to use the composition according to the invention for local administration. The composition could e.g. be locally administered in an arthritic joint Conditions which may be treated by the compositions according to the invention are various forms of autoimmune diseases and tumor diseases e.g. lymphomas and leukemias.

BRIEF DESCRIPTION OF THE DRAWINGS

FIGS. 1A–1C show SEA induced T cell mediated cytotoxicity against RAJI and BSM target cells. The cytotoxicity of an anti-HLA-A2 allospecific T cell line to the RAJI ($HLA\text{-}A2^-DR^+$) and BSM ($HLA\text{-}A2^+DR^+$) lymphoblastoid cell lines in the presence or absence of 1 ng/ml SEA was examined at various effector/target ratios in a standard 4 hour$^{51}$-chromium release assay and is expressed as % specific cytotoxicity.

FIGS. 1A–1C demonstrate the dose-response of SEA at concentrations $10^{-5}$ to $10^{2}$ ng/ml. SEA was added directly into the microtiter wells together with $^{51}$-Chromium labeled RAJI target cells and effector T cells at indicated effector/ target cell ratios. Addition of SEA to the target cells in the absence of effector cells did not result in any significant change in the spontaneous release of $^{51}$-chromium.

Figure 2A:
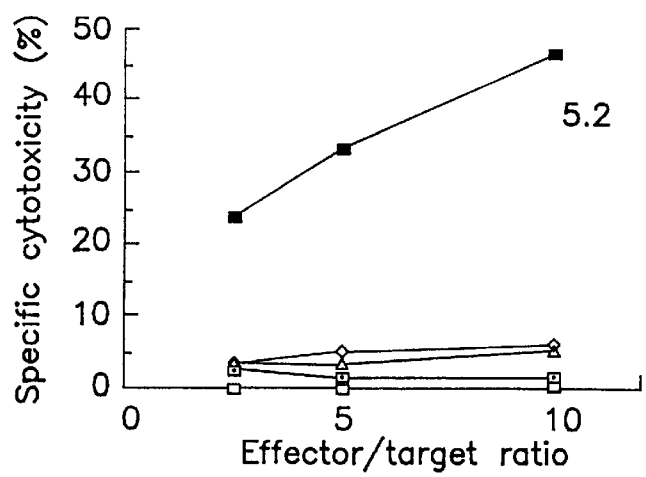
Figure 2B:
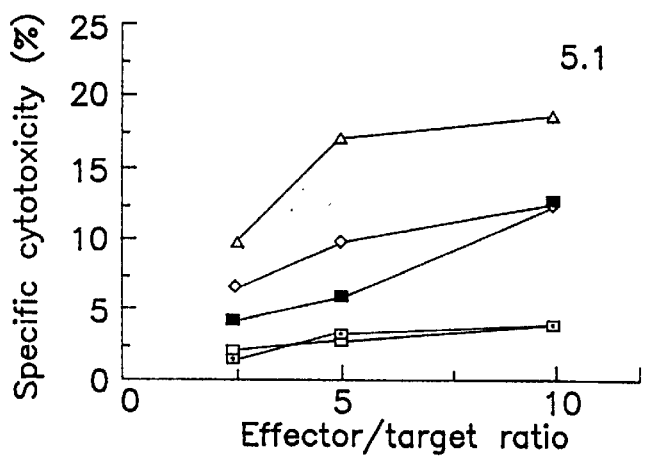
Figure 2C:
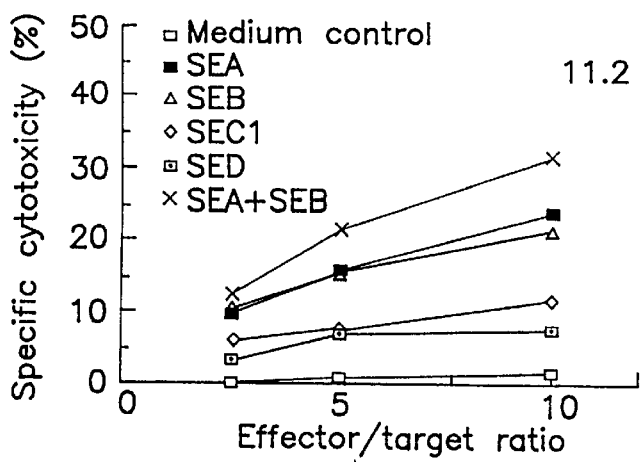

FIGS. 2A–2C show induction of SDCC by SEA, SEB, SEC1 and SED. The cytotoxicity of the anti-HL-A2 allospecific T cell lines 5.2, 5.1 and 11.2 against RAJI target cells in the presence or absence of the various SE at concentration 1 ng/ml was examined in a 4 hour $^{51}$-chromium release assay.

The invention is further illustrated by the following examples which should not be construed as limiting the invention.

EXAMPLES

To determine Staphylococcal enterotoxin directed cell mediated cytotoxicity (SDCC) we employed a panel of human anti-LA-A2 cytotoxic T cell lines as effector cells and the HLA-A2$^-$DR$^+$EBV transformed RAJI B-cell lines the R.2.2 HLA-DR$^-$ mutant of the RAJI cell line and the BLA-A2$^+$DR$^+$BBV transformed BSM B-cell line. The anti-HLA-A2 specific T cell lines were established from primary MLC cultures and repeated restimulations with mitomycin-treated HLA-A2$^+$ stimulator cells and recombinant IL2 (20 units/ml). These T cell lines are strongly lysed the specific HLA-A2 expressing target but not irrelevant targets. The effect of Staphylococcal enterotoxin (SE) A, B, Cl and D was studied using SE from Tox Tech (Madison, Wis., USA). To demonstrate that HLA-DR is the target molecule in SDCC we used the above described panel of target cells and monoclonal antibodies (mAb) directed to HLA-DR, MHC Class II, W6/32 and CD 23.

Chromium Labeling and Incubation of the Target Cells with SEA 0.75×10$^6$ target cells and 150 µCi $^{51}$chromium (Amersham Corp., Arlington Heights, England) were incubated for 45 minutes at 37° C. in a volume of 100 µl. The cells were kept in complete medium containing RPMI-1640 medium (Gibco, Paisley, GBR) supplemented with 2.8% (v/v) 7.5% NaHCO$_3$, 1% sodium pyrovate, 2% 200 mM L-glutamine, 1% 1 M Hepes, 1% 10 mg/ml gentamicin and 10% fetal calf serum (FCS, Gibco, Paisley, GBR). After the incubation the cells were washed once in complete medium without FCS and incubated 60 minutes at 37° C. and washed and resuspended in complete medium containing 10% FCS: 5×10$^3$ target cells were added to each well of U-bottom 96-well microtiter plates (Costar, Cambridge, USA).

Cytotoxicity Assay

The effector cells were added to the wells at various effector/target cell ratios. The final volume in each well was 200 µl. Each test was done in triplicate. The plates were incubated 4 hours at 37° C. after which the released chromium was harvested using SCS Harvesting frames (Skatron, Norway). The amount $^{51}$Cr was determined in a gamma-counter (Cobra Auto-gamma, Packard). The percentage cytotoxicity was computed by the formula % cytotoxicity= (X–M)/(T–M)*100, were X is the chromium release as cpm obtained in the test sample, M is the spontaneous chromium release of target cells incubated with medium, and T is the total chromium release obtained by incubating the target cells with 1% sodium dodecyl sulfate.

Results

Figure 1B:
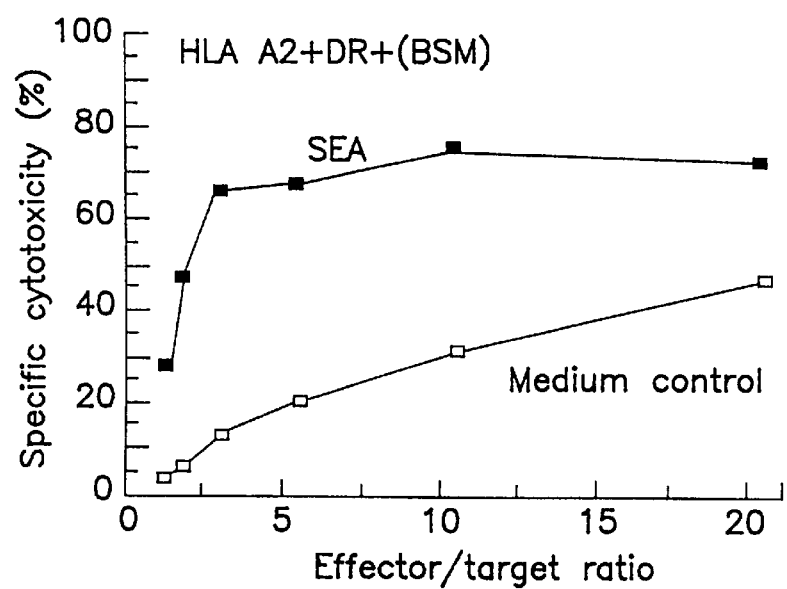
Figure 1C:
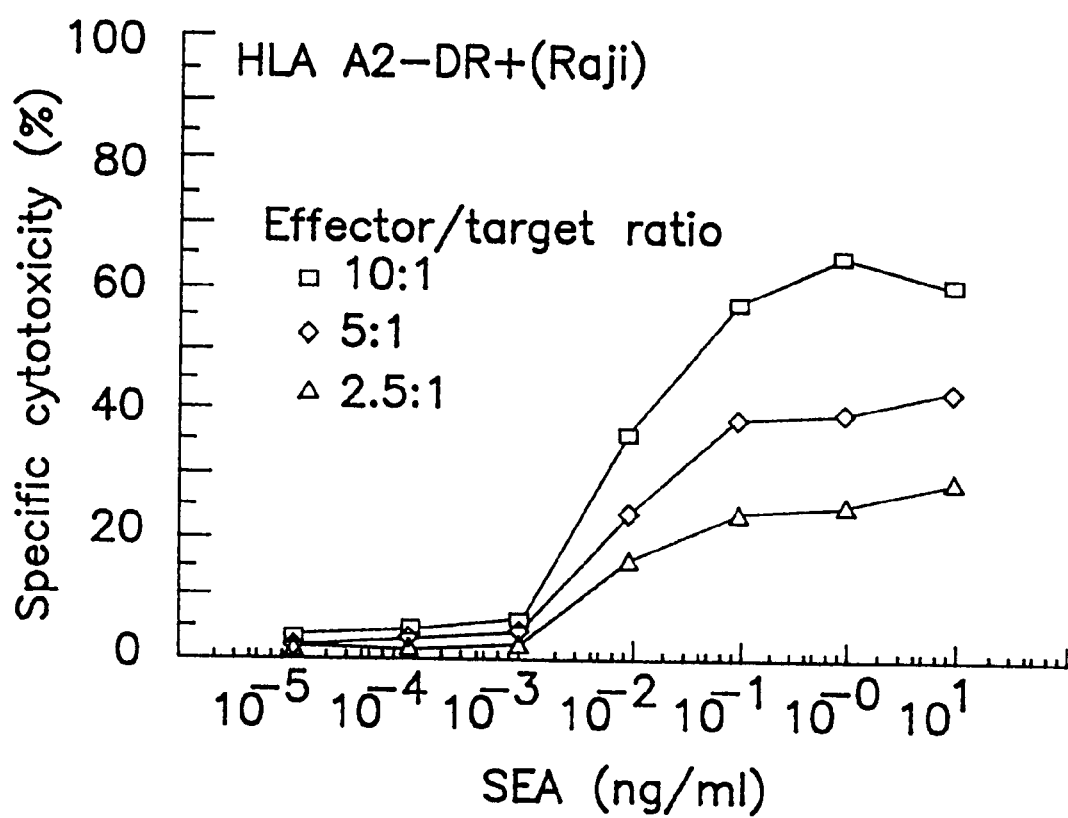

Human allospecific T cell lines, which demonstrated exquisite specificity for HLA-A2 showed strong cytotoxicity against the irrelevant HLA-A2$^-$DR$^+$RAJI target cell and increased cytotoxicity against the specific HLA-A2$^+$DR$^+$BSM target cell, when SEA was added in the assay (FIG. 1A–B). The T cell mediated SE directed cellular cytotoxicity (SDCC) occurred at very low concentrations of SE, with maximal effect at 10–0.1 ng/ml and half maximal effect was seen at about 0.01 ng/ml (FIG. 1C). The SDCC phenomenon could be induced by several of the SE. The 5.2 T cell line showed selective reactivity towards SEA, whereas the 5.1 and 11.2 lines reacted with several SE (FIG. 2A–C). Activation of T cells by the combination of SEA and SEB resulted in an additive increase in cytotoxicity to the RAJI target cell (FIG. 2C). Blocking studies with monoclonal antibodies (mAb) directed to different cell surface structures demonstrated that the mAb GS, which has recently been shown to interact with a SEA binding site on the HLA-DR molecule, strongly inhibited the SDCC (Table 1. Expt #1). In contrast, the HB 96 mAb, which interacts with a monomorphic MHC Class It determinant, unrelated to the SEA binding epitope and the MHC Class I and CD23 mAb did not show any inhibitory activity (Table 1. Expt. #1). Preincubation experiments with SE demonstrated that the binding of SE to the RAJI cells and not to the T cell line was a prerequisite for the induction of SDCC against the RAJI cells (Table 1. Expt.#2). The MHC Class II negative RJ2.2.5 mutant of the RAJI cell line was found to be completely resistant to SDCC, while the Class II expressing parental cell line was an excellent target (Table 1. Expt. #3). These observations implicates that HLA-DR is the main target molecule in SDCC.

TABLE 1

HLA-DR is the target molecule in SDCC

| | | Additive | | % Cytotoxicity at E/T ratio$^A$ | | |
|---|---|---|---|---|---|---|
| Effector | Target | SE | mAb | A | B | C |
| Expt.#1. | | | | | | |
| 5.2 | RAJI | — | — | 1 | 0 | 0 |
| | | + | — | 30 | 19 | 14 |
| | | + | HB96 | 31 | 23 | 16 |
| | | + | G8 | 8 | 6 | 3 |
| | | + | W6/32 | 37 | 28 | 19 |
| | | + | CD23 | 40 | 27 | 19 |
| Expt.#2. | | | | | | |
| 11.2 | RAJI | — | | 2 | 0 | 0 |
| | | + | | 56 | 34 | 14 |
| | RAJI/SE | — | | 33 | 28 | 12 |
| 11.2/SE | RAJI | — | | 2 | 0 | 0 |
| Expt.#3. | | | | | | |
| 12.1 | RAJI | — | | 3 | 2 | 3 |
| | | + | | 43 | 30 | 22 |
| | R12.2.5 | — | | 10 | 11 | 8 |
| | | + | | 12 | 9 | 6 |
| | RAJI/SE | — | | 32 | 24 | 21 |
| | R12.2.5/SE | — | | 12 | 9 | 7 |

$^A$Cytotoxicity of anti-HLA-A2 allospecific T cell lines against HLA-DR$^+$RAJI cells and MHC Class II negative Raji mutant R2.2.5 cells. The different mAb were added at the initiation of the culture at an optimal concentration of 20 ug/ml purified ascites Ig (HB 96 and W6/32) or at a ascites dilution 1/300 (G8 and CD23). SE was added to the assay at 0.1 ng/ml (Expt.#1.), 10 ng/nl (expt #2.) or 1 ng/ml (Expt.#3.). Preincubation of target and effector cells was performed with SE at 1 ng/ml (Expt.#2: RAJI/SE and 11.2/SE) or 10 ng/ml (Expt. #3: RAJI/SE and R.2.2.5/SE) for 30 minutes at room temperature. The cells were extensively washed prior to use in the assay. Addition of SE to the different target cells did not result in any significant change in the spontaneous release of $^{51}$-chromium. The effector/target (E/T) ratios were 20:1, 10:1 and 5:1 in Expt.#1 and #3 and 30:1, 10:1 and 3:1 in Expt.#2.

Composition for Injections 1 ng–100 mg SEA (available from Tox Tech Madison, Wis.) is dissolved in 0, 1–5 ml PBS (Phosphate Buffered Saline) and optionally human serum is albumin or another conventionally used vehicle.

Injections for administration are intravenous bolus injections including 1–5 ml or continuous infusion of 500 ml during a period of 1–24 h.

For demonstration of in Vivo Anti-tumor Effects of SE the Following Two Experimental Approaches are Performed 1. $10^6$ murine MHC II$^{30}$ A20 lymphoma cells in 0.3 ml Saline are injected subcutaneously in C57B1/6 mice. The mice are seated with 1 ug of SEA in 0.5 ml Saline intravenously or as control Saline alone. The treatment is given as one dose every week. Tumor growth is followed every day by measurement of total tumor volume. After 4 weeks of therapy the mice are sacrificed.
2. $10^5$ murine MHC II$^+$ transfected B 16 melanoma cells in 0.3 ml Saline are injected intravenously in C57B1/6 mice. The mice are treated with 1 ug of SEA in 0.5 ml Saline intravenously or as control Saline alone. The treatment is given as one dose every week. Mice are sacrificed after 3 and 4 weeks of therapy and the number of lung metastasis are evaluated.

REFERENCES

1. Guillemot, F., Auffrey, C., Orr, H. T., and Strominger, J.: MHC antigen genes in: Molecular Immunology (Harnes, B. D. and Glover D. M. (Eds.)) pp. 81–143; IRL Press, Oxford, 1988.
2. Bergdoll, M. S.: Enterotoxins In: Staphylococci and Staphyloccocal Infections Vol. II (Easman, C. S. F. and Adlam, C. (Eds.)) pp. 559–598; Acad. Press, New York, 1993.
3. Langford, M. P., Stanton, G. J., Johnson, H. M.: Biological effects of Staphylococcal enterotoxin A on human peripheral blood lymphocytes, Infect. Immun. 22:62–8, 1978.
4. Carlsson, R., Sjogren, H. O.: Kinetics of IL-2 and interferon-gamma production, expression of I2 receptors, and cell proliferation in human mononuclear cells exposed to staphylococcal enterotoxin A, Cell. Immunol. 96:175–181, 1985.
5. Fisher, H., Dohlsten, M., Andersson, U., Hedlund, G., Ericsson, P. E., Hansson, J., Sjogren, H. O.: Production of TNF-a and TNF-b by staphylococcal enterotoxin A activated human T cells. J. Immunol. Methods, in press, 1989.
6. Fisher, H., Dolhsten, M., Lindvall, M., Sjogren, H. O., Carlsson, R.: Binding of staphylococcal enterotoxin A to HLA-DR on B cell lines. J. Immunol. 142: 3151–3157, 1989.
7. Mollick, J. A., Cook, R. G., Rich, R. R.: Class II MHC molecules are specific receptors for staphylococus enterotoxin A. Science 244: 817–820, 1989.
8. Lando, P. A., Dohlsten, M., Kalland, T., Sjogren, H. O., Carlsson, R.: The TCR-CD3 complex is required for activation of human lymphocytes with staphylococcal enterotoxin A. Scand. J. Immunol., in press, 1989.
9. White, J., Herman, A., Pulle, A. M., Kubo, R., Kappler, J. W., Marrack, P.: The Vb-specific superantigen staphylococcal enterotoxin B: Stimulation of mature T cells and clonal deletion in neonatal mice. Cell 56: 27–36, 1989.

We claim:

1. A method of staphylococcal enterotoxin directed cell-mediated cytotoxicity (SDCC) comprising administering a bifunctional crosslinker comprising staphylococcal enterotoxin A to a living body having a target cell expressing an MHC Class II antigen, wherein said bifunctional crosslinker binds to a T cell via a T cell receptor V beta chain and also to a target cell via a Class II MHC antigen, thereby directing cytotoxic T cells to lyse said target cell.

2. A method of lysing a malignant cell expressing MHC Class II antigen composing:

administering a bifunctional crosslinker comprising staphylococcal enterotoxin A to a living body having said cells, wherein said bifunctional crosslinker binds to a T cell via a T cell receptor V beta chain and also to said malignant cell via a Class II MHC antigen, thereby directing cytotoxic T cells to lyse said malignant cell.

* * * * *